(12) United States Patent
Kübler

(10) Patent No.: US 12,233,426 B2
(45) Date of Patent: Feb. 25, 2025

(54) METHOD AND DEVICE FOR HIGH-EFFICIENCY HYDRODYNAMIC SEPARATION OF HEAVY MATERIALS

(71) Applicant: BTA International GmbH, Pfaffenhofen (DE)

(72) Inventor: Hans Kübler, Munich (DE)

(73) Assignee: BTA International GmbH, Pfaffenhofen (DE)

( * ) Notice: Subject to any disclaimer, the term of this patent is extended or adjusted under 35 U.S.C. 154(b) by 0 days.

(21) Appl. No.: 18/682,315

(22) PCT Filed: Jun. 28, 2022

(86) PCT No.: PCT/DE2022/100470
§ 371 (c)(1),
(2) Date: Feb. 8, 2024

(87) PCT Pub. No.: WO2023/016596
PCT Pub. Date: Feb. 16, 2023

(65) Prior Publication Data
US 2024/0342730 A1 Oct. 17, 2024

(30) Foreign Application Priority Data
Aug. 11, 2021 (DE) ...................... 10 2021 004 122.4

(51) Int. Cl.
*B03B 9/06* (2006.01)
*B03B 5/34* (2006.01)
(Continued)

(52) U.S. Cl.
CPC ................. *B03B 9/06* (2013.01); *B03B 5/34* (2013.01); *C12M 23/36* (2013.01); *C12M 29/06* (2013.01); *C12M 47/12* (2013.01)

(58) Field of Classification Search
CPC ............ B03B 9/06; B03B 5/34; C12M 23/36; C12M 29/06; C12M 47/12
(Continued)

(56) References Cited

U.S. PATENT DOCUMENTS 5,377,917 A * 1/1995 Wiljan ................... C12M 45/04
210/603
2011/0253624 A1* 10/2011 Ewing ................... C02F 3/2853
210/607
(Continued)

FOREIGN PATENT DOCUMENTS

CA 2823196 A1 * 2/2014 ............ C12M 21/04
CN 105602844 A * 5/2016
(Continued)

OTHER PUBLICATIONS

International Search Report for PCT/DE2022/100470 dated Oct. 20, 2022.

*Primary Examiner* — Terrell H Matthews
(74) *Attorney, Agent, or Firm* — Buchanan Ingersoll & Rooney PC

(57) ABSTRACT

Important variables which influence the efficiency of a hydrodynamic separation of dense materials using a hydrocyclone are the dynamic viscosity at the inflow of the hydrocyclone and the number of passes through the hydrocyclone. According to the invention, the method and the device allow a control of the viscosity in the hydrocyclone as well as the number of passes through the hydrocyclone when separating dense materials from a slurry in conjunction with an anaerobic fermentation of the constituents of the slurry which can be fermented. By fermenting the constituents of the slurry which can be fermented, the content of a fermentation reactor has a lower viscosity than the slurry being fed. The viscosity in the inflow of the hydrocyclone is set by means of a controlled return flow from a fermentation
(Continued)

reactor, and the number of passes is set by a controlled return flow from the outflow of the hydrocyclone. The slurry is pumped into a return flow from the fermentation reactor. The viscosity in the inflow of the hydrocyclone is controlled by the throughput of the return pump on the basis of the content of solids of the slurry. The number of passes through the hydrocyclone is controlled via the ratio of the feed of the hydrocyclone to the feed of the fermentation reactor from which dense materials are removed. Because the process of diluting the slurry with the content of the fermentation reactor does not have an influence on the hydraulic dwell time in the fermentation reactor, the fermentation reactor can be designed for a smaller accumulation of slurry.

15 Claims, 3 Drawing Sheets

(51) Int. Cl.
*C12M 1/00* (2006.01)
*C12M 1/107* (2006.01)

(58) Field of Classification Search
USPC .......................................................... 209/10
See application file for complete search history.

(56) References Cited

U.S. PATENT DOCUMENTS

| | | | |
|---|---|---|---|
| 2015/0191751 A1 | 7/2015 | Enikeev et al. | |
| 2018/0133721 A1* | 5/2018 | Carra | B03B 13/00 |

FOREIGN PATENT DOCUMENTS

| | | | | |
|---|---|---|---|---|
| DE | 4120808 A1 | 1/1993 | | |
| DE | 102015112254 A1 * | 2/2017 | ............. | B03B 13/00 |
| EP | 0142873 B1 | 5/1985 | | |
| NO | 331292 B1 * | 11/2011 | ......... | B01D 17/0217 |
| WO | 2013160352 A1 | 10/2013 | | |
| WO | WO-2017016718 A1 * | 2/2017 | ............. | B03B 13/00 |

* cited by examiner

METHOD AND DEVICE FOR HIGH-EFFICIENCY HYDRODYNAMIC SEPARATION OF HEAVY MATERIALS

CROSS-REFERENCE TO RELATED APPLICATIONS

The present application is the U.S. national stage application of International Application No. PCT/DE2022/100470, filed on Jun. 28, 2022 claiming priority to German Patent Application No. DE 10 2021 004 122.4, filed Aug. 11, 2021.

FIELD

The invention relates to a method and a device for separating heavy materials from a slurry of components of different densities and different particle structures in conjunction with anaerobic fermentation of the fermentable components of the slurry. The method and device can be configured to ensure a high degree of separation of the heavy materials, regardless of the viscosity or solids content of the slurry.

BACKGROUND

Examples of separation processing for heavy materials can be seen from DE 10 2015 112254 A1 (separation of heavy materials), CN 105 602 844 A (separation process of a suspension for the production of methane), DE 41 20 808 A1 (processing of waste) and EP 0 142 873 A1 (separation of heavy materials from a fermenter), each of which relates to a process for the hydrodynamic separation of heavy materials from a slurry. In each case, a hydrocyclone is used to separate out components with different densities or different particle structures.

During the preparation of substance mixtures of a corresponding humidity, for example organic waste, mechanically separated waste fractions or residues from the food sector, slurries are created, for example pulps or suspensions which still contain relevant amounts of substances which sediment in water and have sharp edges, for example gravel, grit, stones, ceramic or glass fragments, or metal particles. These components cause operational problems in downstream process stages, for example deposits or wear. The consequences include, for example, sediment layers in containers, which require laborious emptying after a few years of operation, laying of pipelines, which requires a lot of cleaning effort, or, as a result of the mostly abrasive properties of these materials, severe wear to the machine technology, which necessitates frequent replacement of worn machine parts.

Organic waste suitable for fermentation may contain heavy mineral materials at for example 4% by weight (Kübler, H., Hoppenheidt, K., Hirsch, P., Kottmair, A., Nimmrichter, R., Nordsieck, H., M., Mücke, W., Swerev (2000) Full scale co-digestion of organic waste. Water Science & Technology 41, 195-202). Municipal organic waste contains significant amounts of heavy mineral materials such as stones, broken glass, grit or gravel, and sand, which according to the studies of Kranert et. al. (Kranert, M., Hartmann A., Graul S. (1999) Determination of sand content in digestate. In: W. Bidlingmaier et al. (Ed.) Proceedings of the International Conference ORBIT 99 on Biological Treatment of Waste and the Environment, Part I, 313-318) can make up a proportion of the dry matter of the waste of sometimes over 25% by weight. When the organic waste is processed, a significant proportion of these heavy mineral substances is introduced into the material flow which is then sent for biological recycling.

During the operation of waste treatment plants in which the screened fraction smaller than 80 mm is sent for processing, a proportion of glass particles and mineral components of 12 to 14% by weight of the wet mass of this fraction was determined in this fraction (Rita, J., Braga, J., Mannail, C., Goldsmith, S., Kübler, H., Rahn, T., Schulte, S. (2015) Compost-like material or thermal valorisation-impact on MBT Plant economics and environmental aspects-case studies in Portugal and UK. In: M. Kühle-Weidemeier and M. Balhar (ed.) Energy and raw materials from residual and organic waste, Cuvillier Verlag Göttingen, 395-406).

In order to ensure unproblematic use of the suspensions from wet processing, the easily sedimenting components are often separated from the suspension. Heavy material separators are used for this. These are based either on sedimentation in the earth's gravitational field or on hydrodynamically generated higher acceleration so as to be able to reduce holding times. The central component of hydrodynamic heavy material separators is often a hydrocyclone (vortex separator).

A vortex separator consisting of two concentric pipes is described in GB 739705. It has no conical portions and the tubes are adjustable along their shared longitudinal axis.

DE 6949940 describes a vortex separator for purifying suspensions, having a tangential inlet, an outlet coaxial with the vortex tube for the purified suspension, and a conically tapering outlet for the precipitated particles.

DE 3427395 describes a method for vortex separation of impurities from problem slurries using a liquid bed. This liquid bed is fluidised by inputting washing water from below and washed out in the vortex separation. Coarser components are removed and finer ones are returned to the vortex separation. The device for carrying out the method consists of a hydrocyclone having a conical lower part to which the washing container is connected.

A flat-base hydrocyclone is described in GB 2076315. It has a coaxial solids discharge into a storage chamber arranged below for the separated solids.

DE 19505073 describes a flat-base hydrocyclone for separating heavy materials from a slurry produced from waste materials. The combination of the flat-base cyclone and the classifying tube increases the selectivity of the heavy material separator. The separated heavy materials are discharged discontinuously in the lower reaches of the classifying pipe using a lock system having a storage chamber. A comparable device is also described in DE 29502488.

EP 1497010 describes a method and device for separating heavy materials in conjunction with a reservoir container. The reservoir container is divided into two zones by a partition. Unpurified suspension is supplied to one zone, and the suspension purified using the heavy material separator is supplied to the other zone. The heavy material separator is fed from the zone having the unpurified suspension. The zone for the purified suspension has an outlet transverse to the main flow direction. The partition is positioned in such a way that, during operation, purified material always flows into the zone having unpurified material, and not the other way around.

EP 3137220 protects a device for hydrodynamic separation of heavy materials consisting of a hydrocyclone, classifying tube and storage chamber having a controlled flushing water flow.

SUMMARY

I have developed methods and devices that can facilitate the regulation of the flushing water flow, the detection of the fill level of the storage chamber and the controlled flooding of the storage chamber.

An important influencing factor for the separation in the hydrocyclone is the dynamic viscosity of the suspension (Trawinski, H. (1995) The separation process in the hydrocyclone Processing technology 36, 410-417). Waste suspensions are often structurally viscous, and if the suspensions are produced from the same waste there is a connection between viscosity and dry residue level or solids content. Tests showed the following relationship between dynamic viscosity η and shear rate γ for different dry residue levels of a suspension:

| Dry residue level [% humidity by mass] | Dynamic viscosity η [mPas] |
|---|---|
| 11.4 | $21900 * \gamma [s^{-1}]^{-0.884}$ |
| 13.5 | $34700 * \gamma [s^{-1}]^{-0.765}$ |
| 18.8 | $21900 * \gamma [s^{-1}]^{-0.706}$ |

For a hydrocyclone, the influence of the solids content of the suspension and the volume flow on the separation efficiency was investigated using a waste suspension (Do Carmo Precci Lopes, A., Senfter, T., Ebner, C., Senn, M., Pillei, M., Kraxner, M., Robra, S. Bockreis, A. (2021) Separation of biodegradable material from low calorific fraction of municipal solid waste. Journal of Cleaner Production 280, 124681). These studies show that the solids content (dry residue level) of the suspension, volume flow and number of passes through the hydrocyclone significantly influence the degree of separation of the heavy materials.

During hydrodynamic separation of heavy materials according to EP 3137220, the reduction of the inorganic sedimenting components of a waste suspension, having a dry residue level of 10.5 to 11.5% based on the wet mass, was determined in a waste fermentation plant using wet mechanical processing for a waste throughput of 12 Mg/h. The results confirm that the number of passes influences the degree of separation.

| | Number of passes | Inorganic sedimenting components [g/kg] | | | |
|---|---|---|---|---|---|
| | | >2 mm | >1 mm | >450 μm | >150 μm |
| Inlet | | 0.942 | 1.684 | 2.246 | 2.830 |
| Outlet | 4.7 | 0.119 | 0.265 | 0.442 | 0.749 |
| Inlet | | 0.803 | 1.575 | 2.251 | 2.903 |
| Outlet | 5.6 | 0.055 | 0.175 | 0.387 | 0.687 |

When moist waste fractions are processed using separation macerators or presses for subsequent fermentation of the fermentable components, waste suspensions having a dry residue level of up to 20% based on their wet mass are produced. Suspensions having such a high dry residue level or solids content have a viscosity which is too high for efficient separation of heavy materials using a hydrocyclone. Reducing the viscosity of a waste suspension by dilution enables efficient use of hydrodynamic separation of heavy materials. However, dilution with additional water increases the volume of the waste suspension and thus causes an increase in the required volume of the downstream fermentation reactor.

During the fermentation of the waste suspension, fermentable components are converted into biogas, which is discharged. The contents of a fermentation reactor therefore have a significantly lower dry residue level or lower viscosity than the supplied waste suspension. Fermentation reactors are usually designed with recirculation, into which the waste suspension is supplied. By mixing the waste suspension with the reactor recirculation, the viscosity can be influenced. If the hydrodynamic separation of heavy materials is integrated into the recirculation of the fermentation reactor, the viscosity in the inlet to the hydrocyclone can be controlled via the mixing ratio of waste suspension to reactor recirculation. This approach was implemented in a plant for the co-fermentation of a waste suspension with sewage sludge (Eisendle, R., Niederkircher, A., Ebner, C. (2016) Novel cyclone technology for the separation of contaminants. KA Betriebs-Info 46, 2444-2446). However, this design has the drawback that only one passage of the waste suspension through the hydrocyclone is possible before entry to the fermentation reactor. This means that only some of the sedimenting heavy materials are separated, and because of the significantly lower viscosity of the contents of the fermentation reactor more sediments form in the container.

To optimise the separation in the hydrocyclone, the supply to the hydrocyclone is controlled via the pressure loss in the hydrocyclone. This determines the volume flow to the heavy material separator. In order to be able to achieve a target value for the viscosity or solids content in the supply, the volume flow of the supplied waste suspension has to be adjusted to the supply to the hydrocyclone. In order to prevent a feedback effect on waste processing, a storage container has to be installed. However, waste suspensions having dry residue levels of up to 20% of the wet mass behave in a viscous manner. Storing them in a container is thus only possible with some difficulty, and still remains problematic.

By contrast, the method according to an embodiment of the invention can ensure optimal operation of a hydrocyclone as a component of a system for separating heavy materials. The solids content in the supply to the hydrocyclone can be adjusted by way of controlled return from a fermentation reactor as well as by way of the number of passes, without any restrictive feedback effect on the upstream process stage for producing the slurry.

Other details, objects, and advantages of the apparatus and method will become apparent as the following description of certain exemplary embodiments thereof proceeds.

BRIEF DESCRIPTION OF THE DRAWINGS

Exemplary embodiments of the invention are explained below with reference to the attached drawings. It should be understood that like reference numbers used in the drawings may identify like components.

Figure 1:
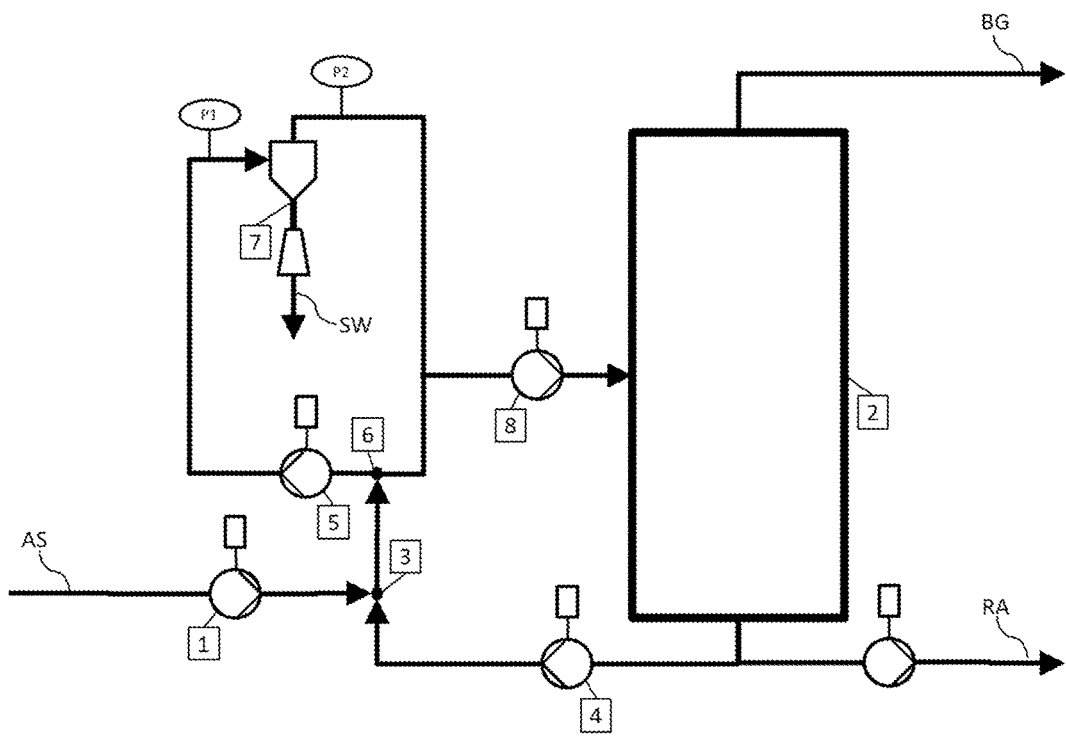
FIG. 1 is a block diagram of an exemplary embodiment of an exemplary embodiment of a device that can implement a method for separation of heavy materials.

Reference numerals used in the drawings include:
AL Exhaust air
AS Slurry/waste suspension
BG Biogas
FFT Solid-liquid separation
RA Reactor discharge
SW Heavy materials
F Flow measurement
L Fill level measurement
P Pressure measurement
V Solids content measurement
1 Supply pump
2 Fermentation reactor
3 Mixing in slurry
4 Return pump
5 Hydrocyclone feed pump
6 Mixing in on suction side of feed pump
7 Hydrocyclone
8 Fermentation reactor feed pump
9 Storage unit
10 Solid-liquid separation feed pump
11 Slurry return pump of solid-liquid separation
12 90° bends
13 Installation region of pressure sensor

DETAILED DESCRIPTION

A corresponding method procedure is shown in FIG. 1. The slurry (waste suspension) is pumped (3) into a return from the fermentation reactor (2) by means of the supply pump (1), the throughput of which is regulated according to the amount of waste suspension produced. The throughput of the return pump (4) is controlled on the basis of a predetermined ratio to the throughput of the supply pump (1) in order to achieve the required reduction in solids content. The resulting mixture, which has a lower solids content than the waste suspension, is supplied (6) to the suction side of the hydrocyclone feed pump (5). The throughputs of the hydrocyclone (7) and its feed pump are a multiple of the sum of the throughputs of the supply pump (1) and the return pump (4) combined, so as to enable several passes of the waste suspension through the separation of heavy materials before it is supplied to the fermentation reactor. The throughput of the feed pump (5) is regulated by means of pressure measurement (P1) in the inlet of the hydrocyclone (7). The suspension which has been freed of heavy materials in the hydrocyclone is returned to the suction side of the hydrocyclone feed pump (5). To ensure a constant pressure loss in the hydrocyclone, the delivery rate of the fermentation reactor feed pump (8) is regulated by means of the pressure measurement (P2) in the outlet of the hydrocyclone (7), in such a way that the pressure difference P1-P2 is constant.

Figure 2:
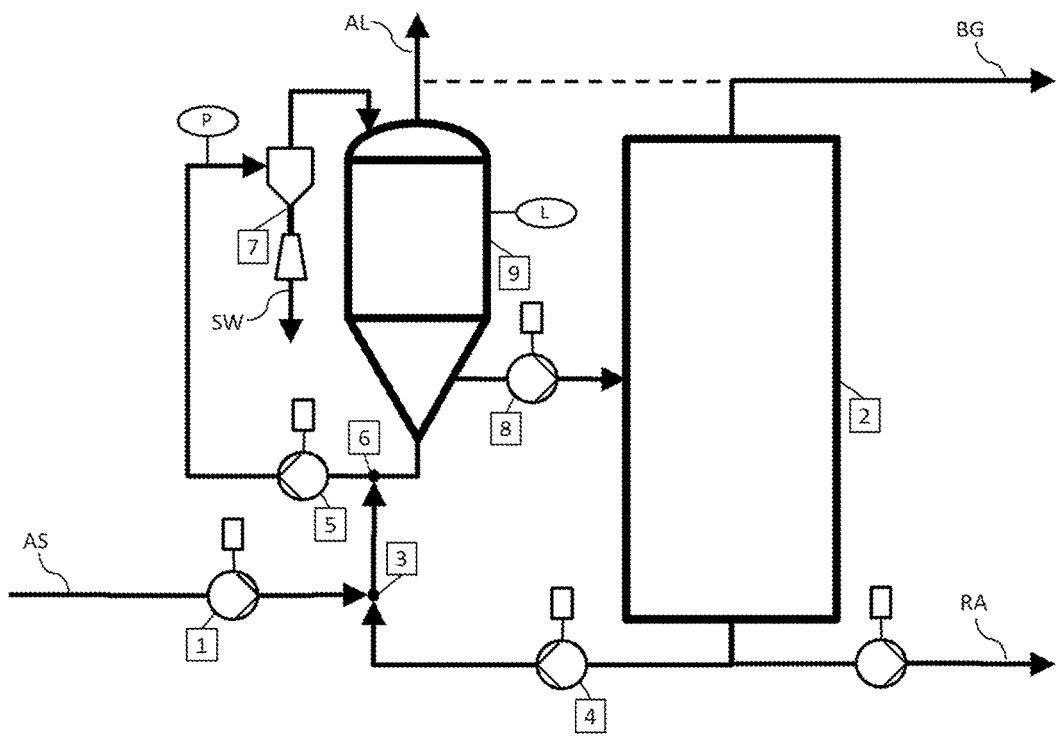
FIG. 2: is a block diagram of an exemplary embodiment of an exemplary embodiment of a device that can implement a method for separation of heavy materials.

Integrating a storage unit into the outlet of the hydrocyclone enables more stable control (see FIG. 2). As a result of the free overflow of the hydrocyclone (7) into the reservoir (9), only one pressure measurement (P) in the inlet of the hydrocyclone is required so as to ensure a constant pressure loss in the hydrocyclone. If the fill level (L) in the storage unit (9) allows it, the fermentation reactor feed pump (8) is controlled on the basis of a predetermined ratio to the throughput of the hydrocyclone feed pump (5), so as to implement a predetermined number of passes through the separation of heavy materials. If a predetermined upper fill level is exceeded in the storage unit (9), the throughput of the fermentation reactor feed pump (8) is regulated as a function of the fill level (L) in the storage unit (9), until the upper fill level in the storage unit (9) is undershot again. The throughput of the fermentation reactor feed pump (8) is then controlled on the basis of the throughput of the feed pump (5) of the system for separating heavy materials.

The storage unit (9) is preferably connected to the exhaust air treatment system. If formation of relevant amounts of methane or hydrogen is expected as a result of anaerobic biological activity in the storage unit, the storage unit should be connected to the biogas collection (FIG. 2, dashed line) to improve the biogas yield from the fermentation.

The throughputs of the pumps are controlled via the speed of each pump. In the simple implementation of the method using a storage unit, the speed specifications are determined as follows:

The speed of the supply pump (1) is controlled as a function of the accumulating volume of waste suspension.

The required speed of the return pump (4) is determined on the basis of:
throughput of the supply pump, calculated using the speed of the supply pump, the discharge head determined from the inventory, and the pump characteristic curve stored in the control system,
required throughput of the return pump, which is calculated using the ratio of the average dry residue levels in the waste suspension and the return (dry residue levels determined in samples in the laboratory) and the dry residue level which is to be achieved in the mixture of these two material flows and
required speed of the return pump, which is calculated from the required throughput using a specified discharge head and the pump characteristic curve stored in the control system.

The speed of the feed pump (5) for the separation of heavy materials is controlled by measuring the pressure in the inlet of the hydrocyclone (P) in order to ensure the specified pressure loss in the hydrocyclone.

In the event that the fill level in the storage unit (9) is below a predetermined upper fill level, the required speed of the fermentation reactor feed pump (8) is determined on the basis of:
throughput of the hydrocyclone feed pump (5) is calculated using the speed of the feed pump, the discharge head determined from the inventory, pressure loss in the hydrocyclone, and the pump characteristic curve stored in the control system,
required throughput of the fermentation reactor feed pump (8), which is calculated using the throughput of the hydrocyclone feed pump (5) and the predetermined number of passes through the hydrocyclone and
required speed of the fermentation reactor feed pump (8), which is calculated from the required throughput using the discharge head determined from the inventory and the pump characteristic curve stored in the control system.

In the event that the fill level in the storage unit (9) is above a predetermined upper fill level, the required speed of the fermentation reactor feed pump (8) is regulated by means of the fill level measurement (L) in the storage unit, in such a way that the fill level slowly drops until it falls below the specified upper fill level.

Figure 3:
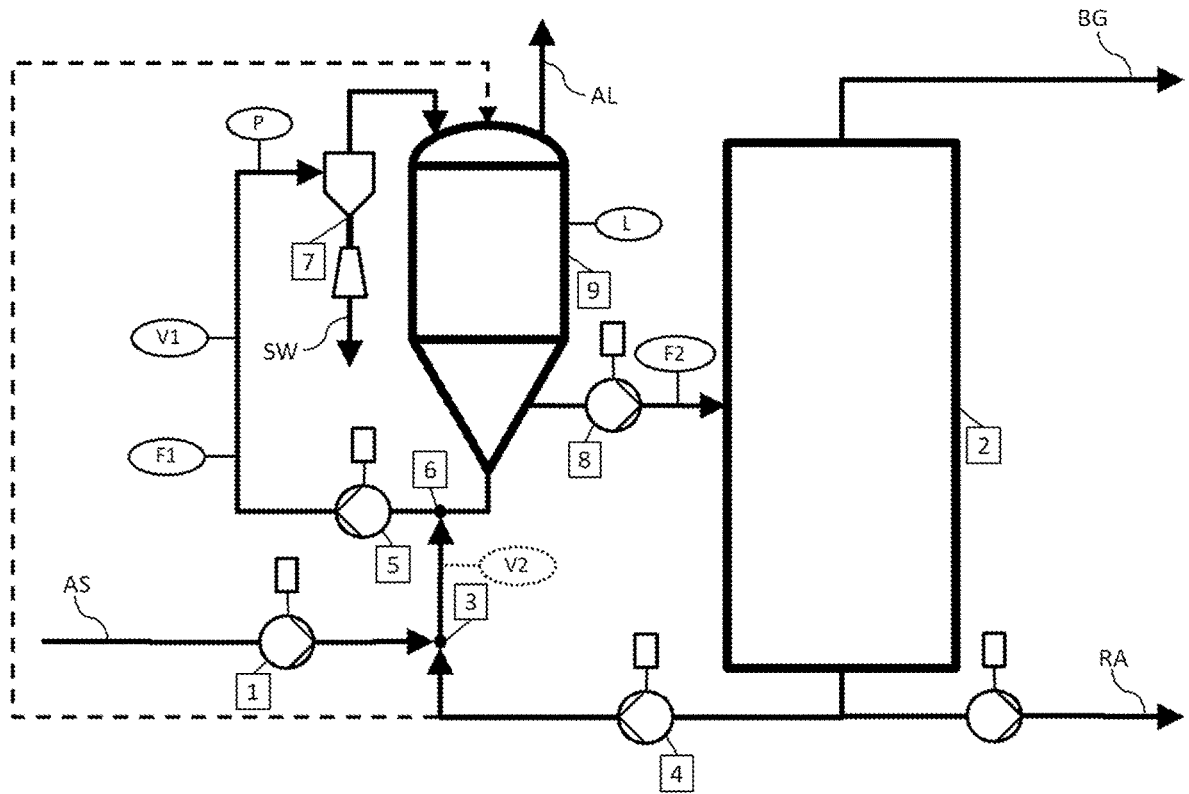
FIG. 3: is a block diagram of an exemplary embodiment of an exemplary embodiment of a device that can implement a method for separation of heavy materials.

A preferred embodiment of the method is equipped with additional measurement technology (FIG. 3). In the supply to the hydrocyclone, the solids content of the suspension (V1) is measured as a guide to the dry residue level or viscosity of the suspension. As a function of this measured value, the speed of the return pump (4) is regulated in such a way that the measured solids content corresponds to the setpoint specified by the control system. Alternatively, the solids content can also be measured in the mixture of waste suspension and return (V2) if this enables better control behaviour. Furthermore, flow measurement systems are installed in the supply (F1) to the hydrocyclone and in the supply (F2) to the fermentation reactor. As a result, if the fill level in the storage unit (9) is below a predetermined upper fill level, the speed of the fermentation reactor feed pump (8) can be regulated in such a way that a predetermined ratio of F1 to F2 is maintained. This ratio approximately corresponds to the number of passes through the system for separating heavy materials, since the mass of the separated heavy materials (SW) is negligible by comparison with the masses of the volume flows F1 and F2.

Figure 4:
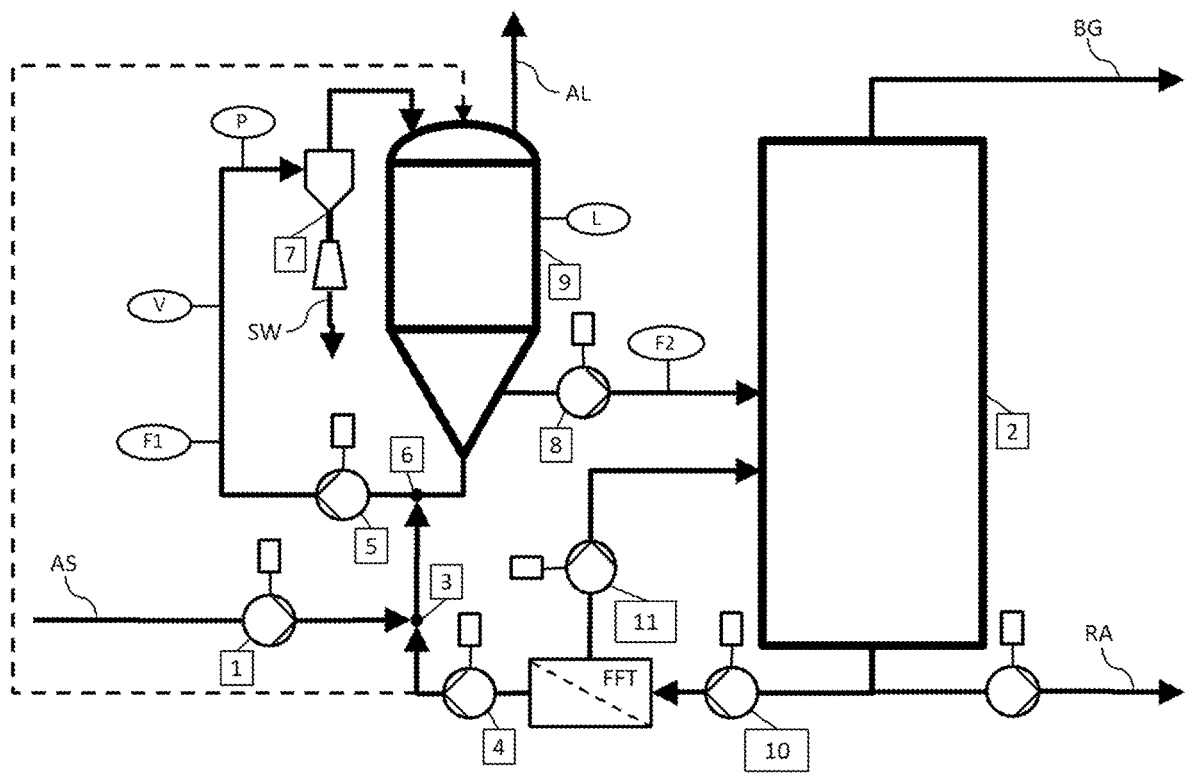
FIG. 4: is a block diagram of an exemplary embodiment of an exemplary embodiment of a device that can implement a method for separation of heavy materials.

For setting the dry residue level required for optimal separation of heavy materials, the required return can be very high, as a result of the dry residue level in the fermentation reactor. If this causes the hydraulic load on the hydrocyclone to become too high, a second heavy material separator is required. In this case, the dry residue level in the volume flow to be returned can be reduced using solid-liquid separation. FIG. 4 shows the method according to an exemplary embodiment of the invention with the necessary additions. A solid-liquid separation (FFT) is fed from the fermentation reactor (2) using a pump (10), and separates off a large part of the solids, which mainly contribute to a higher viscosity, at a consistency which can still be pumped. These are then returned to the fermentation reactor using a pump (11). By way of the return pump (4), the generated material flow, which is characterised by a lower dry residue level or lower viscosity than the contents of the fermentation reactor, is returned for blending with the waste suspension (3). As a result of the reduced dry residue level of the material from the fermentation reactor returned for separation of heavy materials, the return pump (4) has to supply less to the separation of heavy materials so as to set the required dry residue level in the inlet of the hydrocyclone (7). This means that an increase in the separation of heavy materials can be avoided or the specified number of passes can be achieved by maintaining the hydraulic load on the hydrocyclone.

By returning a liquid phase, which has been freed of filterable substances by the solid-liquid separation, using the return pump (4), the entry of methanogenic microorganisms into the storage unit (9) is also reduced. This largely prevents the formation of methane and hydrogen in the storage unit. This promotes a connection of the storage unit to the exhaust air treatment system, which brings about operational advantages and can be implemented more cost-effectively.

An advantage of the method procedures described above is that the waste suspension is diluted using contents of the fermentation reactor. This dilution therefore has no influence on the hydraulic holding time nor on the solids holding time in the fermentation reactor. The fermentation reactor can therefore only be designed for the significantly smaller accumulation of waste suspension.

Some embodiments can be implemented as follows:

In the aforementioned waste fermentation plant, the dry residue level of the waste suspension is approximately 11% based on the wet mass (FM) for an accumulation of 37 Mg/h. The dry residue level in the fermentation reactor is approximately 6% by wet mass. Do Carmo Precci Lopes et al. (2021) recommend, in their publication, a dry residue level of 9% by wet mass in the inlet of the hydrocyclone. This dry residue level can be set, in the method procedure described in FIG. 1, after combining the waste suspension and recycling in point 3 by returning 25 Mg of contents of the fermentation reactor per hour. If the dry residue level in the inlet and outlet of the hydrocyclone changes only negligibly as a result of the separation of heavy materials, the dry residue level in the supply to the hydrocyclone corresponds to this value. For a throughput of 310 Mg/h through the system for separating heavy materials, 5 passes through the hydrocyclone can be implemented.

If the dry residue level changes significantly during passage through the hydrocyclone, a method procedure analogous to FIG. 3 is preferable. If the separation of heavy materials separates off 10% of the dry residue level of the waste suspension, the return pump (4) only has to pump 15 Mg of the fermentation reactor's contents per hour in order to maintain the desired dry residue level of 9% by wet mass in the hydrocyclone inlet. In this case, only 260 Mg/h need to be supplied to the hydrocyclone for 5 passes.

If 37 Mg/h of a waste suspension having a dry residue level of 17% by wet mass is supplied into this process and 10% thereof is separated during the separation of heavy materials, at a dry residue level of 6% by wet mass, 88 Mg/h must be returned to the fermentation reactor in order to set a dry residue level of 9% by wet mass in the inlet of the hydrocyclone. To achieve a number of passes through the hydrocyclone of five, 625 Mg/h must be supplied thereto.

If, in this case, the method procedure is carried out analogously to FIG. 4 and the dry residue level in the return can be reduced to 2% by wet mass using the solid-liquid separation, only 36 Mg/h must be returned to set the dry residue level in the hydrocyclone inlet to 9% by wet mass. As a result, a throughput of 365 Mg/h through the separation of heavy materials enables a number of passes of five.

Since the number of required passes through the hydrocyclone is largely determined by the ratio of the supply flow for separating heavy materials to the feed flow for fermentation, the usable volume of the storage unit (9) has no influence on it. As a result of the mixing of the waste suspension with contents of the fermentation reactor, this mixture is characterised by methanogenic activity. In order to limit the formation of biogas in the storage unit, the usable volume of the storage unit is limited to ensure the shortest possible holding time. In a preferred embodiment of the method according to the invention, the usable volume of the storage unit is only 1 to 2 times the volume of waste suspension supplied per hour.

Centrifugal pumps are preferably used as the supply pump (1) and feed pump (5) for the separation of heavy materials, as they are available in a very robust and low-wear design. As a result of the hydrostatic pressure in the fermentation reactor and the reduced content of heavy materials in the material flows to be conveyed, the feed pump (8) for the fermentation reactor and the return pump (4), provided that it draws directly from the reactor, are designed as positive displacement pumps.

In a method design according to FIG. 1 or FIG. 2, depending on the operating and installation situation, the design of the return pump as a positive displacement pump may require that the supply pump be designed as a positive displacement pump. In the method design according to FIG. 3, this can be avoided. If the return pump is controlled by measuring the solids content of the suspension (V1) in the hydrocyclone inlet, the return can be supplied directly (dashed line) to the storage unit (9).

For a method procedure analogous to FIG. 4, the solid-liquid separation feed pump (10) and the pump for returning the solids (11) are positive displacement pumps. In this case, the return pump (4) may be designed as a more cost-effective and lower-wear centrifugal pump. A return (dashed line) directly into the storage unit (9) simplifies the configuration of the return pump and improves the control behaviour, since the back pressure of the return pump changes solely as a function of the delivery rate of this pump.

Figure 5:
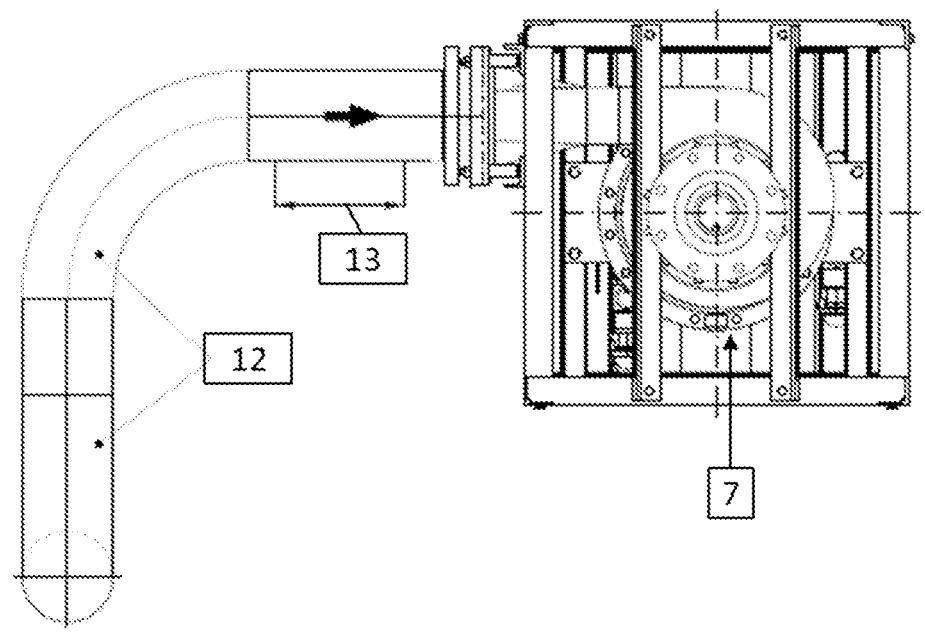
FIG. 5: is a schematic illustration of an exemplary embodiment of a hydrocyclone.

In the supply to the hydrocyclone, two 90° bends (12) cause the supply flow to be diverted from the vertical flow direction into a horizontal flow direction, and then horizontally, before entering the hydrocyclone. This ensures that the heavy materials are introduced largely tangentially at the wall of the hydrocyclone. The pressure measurement sensor is installed in the supply line laterally just before the hydrocyclone on the opposite side (13), to reduce abrasion. Furthermore, it does not protrude into the suspension flow, but rather is installed offset back a few millimetres from the inner pipe wall to improve its service life (FIG. 5).

The mixture of slurry and return from the fermentation reactor is supplied on the suction side of the feed pump (5) of the system for separating heavy materials. This ensures that this centrifugal pump provides good mixing of the three material flows supplied to the hydrocyclone.

While certain exemplary embodiments of the method, device, and apparatus and methods of making and using the same have been shown and described above, it is to be distinctly understood that the invention is not limited thereto but may be otherwise variously embodied and practiced within the scope of the following claims.

The invention claimed is:

1. A method for hydrodynamically separating heavy materials of a slurry having components of different density using a hydrocyclone, said slurry, after the separation of the heavy components, being supplied to a fermentation reactor for fermentation of fermentable components of said slurry, the slurry being mixed with the material of a controlled return of content from the fermentation reactor to form a substrate supply to the hydrocyclone so as to achieve a reduction in solids content, characterized in that a suspension freed of heavy materials, from the hydrocyclone, is further mixed into the substrate supply for feeding to the hydrocyclone by returning from the hydrocyclone into the mixture of slurry and fermentation reactor content so as to allow a plurality of passes of the slurry through the hydrocyclone before it is supplied to the fermentation reactor in such a way that the supply flow for heavy materials separation is at least two times greater than the mass flow of the mixture of slurry and return from the fermentation reactor and in that throughput through the hydrocyclone is regulated by measuring a pressure in an inlet of the hydrocyclone in such a way that this pressure is kept constant and a delivery rate of a feed pump being controlled via a pressure sensor installed on an inside of a flow profile created by the second bend;
wherein the slurry is diverted from a vertical flow direction into a horizontal flow direction using a first 90° bend and is then diverted horizontally using a second 90° bend prior to the slurry entering the hydrocyclone.

2. The method of claim 1, wherein a suspension freed of the heavy components from the hydrocyclone is stored in a storage unit prior to being supplied to the fermentation reactor or being supplied to the mixture of slurry and return from the fermentation reactor, a pressure measurement being taken in the inlet of the hydrocyclone to ensure a constant pressure loss in the hydrocyclone.

3. The method of claim 1, wherein a return flow from the fermentation reactor is controlled as a function of a speed of a supply pump for the slurry, a solids content of the slurry, and a solids content of the return flow from the fermentation reactor.

4. The method of claim 1, wherein that a return flow from the fermentation reactor is controlled by measuring the solids content in the supply to the heavy components separation.

5. The method of claim 1, wherein a supply to the fermentation reactor is controlled by measuring a supply flow to the separation of the heavy components.

6. The method of claim 1, wherein a solids content of a material flow returned from the fermentation reactor to the separation of heavy components is reduced by way of solid-liquid separation so that solids separated via the solid-liquid separation are returned into the fermentation reactor.

7. A device for processing a slurry having components of different density in connection with an anaerobic fermentation of fermentable components of the slurry in a fermentation reactor and a hydrocyclone provided for hydrodynamically separating heavy materials of the slurry, said device comprising:
a substrate supply line to the hydrocyclone, into which
a) a mix line of both slurry and return content from the fermentation reactor opens, and
b) a suspension line for a suspension freed of heavy materials from the hydrocyclone,
the substrate supply line being configured so that a plurality of passes of the slurry through the hydrocyclone is provided for operation of the hydrocyclone via the substrate supply line to the hydrocyclone,
wherein a throughput through the hydrocyclone is regulated by measuring a pressure in an inlet of the hydrocyclone in such a way that the pressure in the inlet is kept constant and a supply flow for heavy components separation is at least two times greater than a mass flow of a mixture of slurry and return content from the fermentation reactor,
wherein the device is configured so that the slurry, prior to entry to the hydrocyclone, is diverted from a vertical flow direction into a horizontal flow direction using a first 90° bend, and then diverted horizontally using a second 90° bend, and
a pressure sensor for controlling a feed pump is installed on an inside of a flow profile created by the second 90° bend.

8. The device of claim 7, comprising:
a sensor for measuring the solids content installed in the supply line to the hydrocyclone for controls the delivery rate of the return pump from the fermentation reactor.

9. The device of claim 7, comprising:
at least one flow meter installed in the supply line to the hydrocyclone and/or in the supply line to the fermentation reactor.

10. A device for processing a slurry having components of different density in connection with an anaerobic fermentation of fermentable components of the slurry in a fermentation reactor and a hydrocyclone provided for hydrodynamically separating heavy materials of the slurry, said device comprising:
a substrate supply line to the hydrocyclone, into which
a) a mix line of both slurry and return content from the fermentation reactor opens, and
b) a suspension line for a suspension freed of heavy materials from the hydrocyclone, the substrate supply line being configured so that a plurality of passes of the slurry through the hydrocyclone is provided for operation of the hydrocyclone via the substrate supply line to the hydrocyclone,
wherein a throughput through the hydrocyclone is regulated by measuring a pressure in an inlet of the hydrocyclone in such a way that a pressure difference between a pressure in the inlet and a pressure measurement of an outlet of the hydrocyclone is kept constant, and a delivery rate of a fermentation reactor feed pump being regulated by means of the pressure measurement in the outlet of the hydrocyclone in such a way that the pressure difference is constant; and
wherein the device is configured so that the slurry, prior to entry to the hydrocyclone, is diverted from a vertical flow direction into a horizontal flow direction using a 90° bend, and then diverted horizontally using a 90° bend, and a pressure sensor for controlling the feed pump is installed on an inside of a flow profile created by the second bend.

11. The device of claim 7, comprising:
a storage unit that is integrated into the outlet of the hydrocyclone.

12. The device of claim 11, wherein the storage unit is connected to an exhaust air treatment system.

13. The device of claim 7, wherein throughput through the hydrocyclone is regulated by measuring the pressure in the inlet of the hydrocyclone and the pressure in the outlet of the hydrocyclone in such a way that a pressure difference remains constant.

14. The device of claim 7, wherein the device is configured to take a pressure measurement in the inlet of the hydrocyclone to ensure a constant pressure loss in the hydrocyclone.

15. A method of for hydrodynamically separating heavy materials of a slurry, the method comprising:
using a hydrocyclone for processing said slurry to separate components of the slurry that are above a pre-selected density from the slurry, the components that are above the pre-selected density being the components of the slurry that are defined as being heavy components;
supplying the slurry to a fermentation reactor for fermentation of fermentable components of said slurry after the heavy components are separated from the slurry,
mixing the slurry with a material of a controlled return of content from the fermentation reactor to form a substrate supply for feeding to the hydrocyclone so as to achieve a reduction in solids content, characterized in that a suspension freed of the heavy components from the hydrocyclone is further mixed into the substrate supply for feeding to the hydrocyclone so as to allow a plurality of passes of the slurry through the hydrocyclone before it is supplied to the fermentation reactor in such a way that the supply flow for heavy components separation is at least two times greater than a mass flow of the mixture of slurry and return from the fermentation reactor and in that throughput through the hydrocyclone is regulated by measuring a pressure in an inlet of the hydrocyclone in such a way that the pressure in the inlet is kept constant;
diverting the slurry from a vertical flow direction into a horizontal flow direction using a first 90° bend prior to the slurry entering the hydrocyclone, and then diverting the slurry horizontally using a second 90° bend; and
regulating a delivery rate of a feed pump via utilizing a pressure sensor installed on an inside of a flow profile created by the second bend for controlling the feed pump.

* * * * *